(12) United States Patent
Schickaneder et al.

(10) Patent No.: US 8,809,549 B2
(45) Date of Patent: Aug. 19, 2014

(54) ESTERS OF BENDAMUSTINE AND RELATED COMPOUNDS, AND MEDICAL USE THEREOF

(71) Applicant: Arevipharma GmbH, Radebuel (DE)

(72) Inventors: Helmut Schickaneder, Eckental (DE); Armin Buschauer, Lappersdorf (DE); Guenther Bernhardt, Schierling (DE); Christian Schickaneder, Lauf a. d. Pegnitz (DE); Michael Limmert, Dresden (DE); Stefan Huber, Regensburg (DE)

(73) Assignees: Helmut Schickaneder (DE); Christian Schickaneder (DE)

( * ) Notice: Subject to any disclaimer, the term of this patent is extended or adjusted under 35 U.S.C. 154(b) by 0 days.

(21) Appl. No.: 13/870,759

(22) Filed: Apr. 25, 2013

(65) Prior Publication Data
US 2013/0289032 A1 Oct. 31, 2013

Related U.S. Application Data

(60) Provisional application No. 61/638,535, filed on Apr. 26, 2012.

(30) Foreign Application Priority Data

Apr. 26, 2012 (EP) .................................... 12165728

(51) Int. Cl.
C07D 235/16 (2006.01)
C07D 401/12 (2006.01)
C07D 403/12 (2006.01)
C07D 413/12 (2006.01)
A61K 31/4184 (2006.01)
C07D 235/12 (2006.01)

(52) U.S. Cl.
CPC ............ *C07D 235/16* (2013.01); *C07D 235/12* (2013.01)
USPC ...................... 548/306.1; 548/309.7; 546/199; 544/139; 544/370; 514/234.5; 514/254.06; 514/322; 514/394

(58) Field of Classification Search
USPC ............................................ 548/306.1, 309.7
See application file for complete search history.

(56) References Cited

U.S. PATENT DOCUMENTS

| | | | |
|---|---|---|---|
| 2012/0003305 A1 | 1/2012 | Colledge et al. | |
| 2012/0165543 A1 | 6/2012 | Groh et al. | |

FOREIGN PATENT DOCUMENTS

| | | |
|---|---|---|
| CN | 101691359 A | 4/2010 |
| DE | 10 2010 055 499 A1 | 6/2011 |
| WO | WO 2009/120386 A2 | 10/2009 |
| WO | WO 2010/042568 A1 | 4/2010 |
| WO | WO 2011/079193 A2 | 6/2011 |
| WO | WO 2011/151086 A1 | 12/2011 |

OTHER PUBLICATIONS

Extended Search Report issued in European Patent Application No. 12 16 5728, mailed Jun. 2, 2012, 8 pages.
Scutaru et al., "Bivalent bendamustine and melphalan derivatives as anticancer agents," European Journal of Medicinal Chemistry, vol. 46, pp. 1604-1615, May 2011.
Scutaru et al., "Optimization of the N-Lost Drugs Melphalan and Bendamustine: Synthesis and Cytotoxicity of a New Set of Dendrimer-Drug Conjugates as Tumor Therapeutic Agents", Biconjugate Chem., vol. 21, pp. 1728-1743, 2010.
Werner et al., "Hydrolyseprodukte des Cancerostaticums Cytostasan (Bendamustin)," Pharmazie, vol. 42, pp. 272-273, 1987.

*Primary Examiner* — Laura L. Stockton
(74) *Attorney, Agent, or Firm* — Schwegman, Lundberg & Woessner, P.A.

(57) ABSTRACT

The present invention relates to particular esters of bendamustine and related compounds, and medical uses thereof.

8 Claims, No Drawings

ESTERS OF BENDAMUSTINE AND RELATED COMPOUNDS, AND MEDICAL USE THEREOF

CROSS-REFERENCE TO RELATED APPLICATIONS

The present application for patent is based upon and claims priority to U.S. Provisional Application No. 61/638,535 and European Application No. 12165728.2, both filed on Apr. 26, 2012, the entire specifications, claims and drawings of which are incorporated herewith by reference.

FIELD OF THE INVENTION

The present invention relates to esters of bendamustine and related compounds, and medical uses thereof.

BACKGROUND OF THE INVENTION

Bendamustine having the structural formula

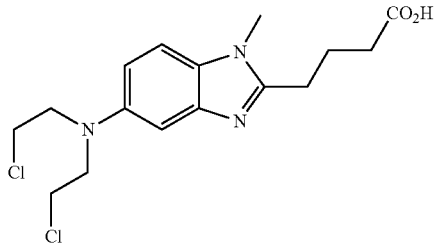 [SMILES: Cn1c(CCCC(=O)O)nc2cc(N(CCCl)CCCl)ccc21]

is a nitrogen mustard belonging to the family of drugs called alkylating agents. Bendamustine has been shown to be effective in the treatment of chronic lymphocytic leukemias and lymphomas. Bendamustine is normally used in its hydrochloride salt form as active agent. However, efficacy in terms of cytotoxicity and/or cytostaticity is a challenging issue and a critical problem.

US 2012/0003305 A1 and WO 2011/151086 A1 disclose pharmaceutical compositions of bendamustine or derivatives thereof for oral administration which comprise a pharmaceutically acceptable ingredient in the form of non-ionic surfactant(s) selected from the group consisting of polyethoxylated castor oil or derivatives thereof and block copolymer of ethylene oxide and propylene oxide, wherein in the compositions of WO 2011/151086 A1, alternatively to the aforementioned non-ionic surfactant(s), the pharmaceutically acceptable ingredient may be saccharide(s) selected from the group consisting of monosaccharide(s), disaccharide(s), oligosaccharide(s), cyclic oligosaccharide(s), polysaccharide(s) and saccharide alcohol(s). These non-ionic surfactant(s) or saccharide(s) are added to the pharmaceutical composition in order to avoid or reduce degradation of bendamustine in the form of the free acid within the pharmaceutical composition, and in particular to avoid degradation in the small or large intestine after uptake of bendamustine in order to improve its bioavailability. Besides the typical undesired degradation products of bendamustine in the form of the free acid, namely [5-[(2-chloroethyl)-(2-hydroxyethyl)amino]-1-methyl-benzimidazo-2-yl]-butanoic acid, 4-[5-Bis(2-hydroxyethyl)amino]-1-methylbenzimidazol-2-yl]-butanoic acid and 4-(5-morpholino-1-methylbenzimidazol-2-yl)-butanoic acid, for formulation purposes, bendamustine may also be present in the form of esters with sugar alcohols and C1-C6 alkyl alcohols.

WO 2010/042568 A1 discloses the preparation of pure bendamustine methyl ester

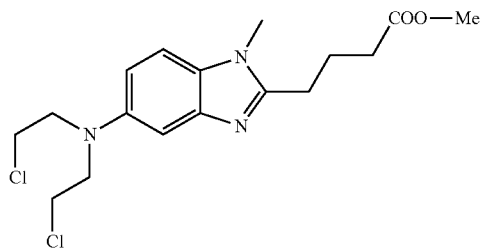

as starting material for the preparation of bendamustine hydrochloride.

CN 10169359 A discloses a process for preparing bendamustine hydrochloride in which bendamustine ethyl ester is obtained in form of a crude product which is further converted without purification. WO 2009/120386 A2 discloses a process for preparing bendamustine hydrochloride in which bendamustine ethyl ester is used as the starting material, wherein the document remains silent on preparation and purity of the applied bendamustine ethyl ester.

WO 2011/079193 A2 discloses the preparation of pure bendamustine isopropyl ester as starting material for the preparation of bendamustine hydrochloride.

A. M. Scutaru et al., "Bivalent bendamustine and melphalan derivatives as anticancer agents", European Journal of Medical Chemistry, Vol. 46 (2011), pages 1604 to 1615 mainly focus on a concept of bivalent drugs and in this content show cytotoxicity data for maleimide-coupled bivalent bendamustine compounds comprising two moieties derived from bendamustine ester formed with N-(2-hydroxy-ethyl)maleimide. These bivalent bendamustine compounds are compared with bendamustine and a monovalent bendamustine ester formed with N-(2-hydroxy-ethyl)maleimide.

M. Scutaru et al., "Optimization of the N-Lost Drugs Melphalan and Bendamustine: Synthesis and Cytotoxicity of a New Set of Dendrimer-Drug Conjugates as Tumor Therapeutic Agents", Bioconjugate Chem., 2010, 21, pages 1728 to 1743 disclose among others that modification of bendamustine with an N-(2-hydroxyethyl)maleimide spacer increases the hydrolytic stability of the N-lost moiety of bendamustine. There is still a need for bendamustine derivatives, and thus an object of the present invention is to provide bendamustine related compounds with useful properties and therapeutical effects, and therapeutic uses thereof.

SUMMARY OF THE INVENTION

The object is solved by a compound of formula I according to claim 1 and a compound of formula II according to claim 7. Preferred embodiments are set forth below and in the subclaims.

Various aspects, advantageous features and preferred embodiments of the present invention as summarized in the following items, respectively alone or in combination, contribute to solving the object of the invention:

(1) A compound of formula I

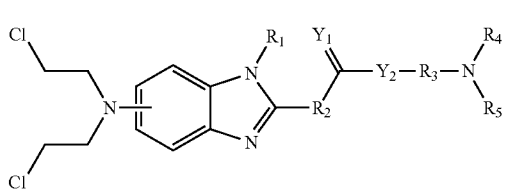

or a pharmaceutically acceptable salt thereof,
wherein $R_1$ is alkyl, aryl or alkylaryl; $R_2$ and $R_3$ independently from each other represent alkanediyl, arylene, alkylarylene, alkylene or arylalkanediyl; $Y_1$ and $Y_2$ independently from each other represent oxygen or sulphur; and $R_4$ and $R_5$ independently from each other represent substituted or unsubstituted alkyl; optionally, $R_4$ and $R_5$ together represent a C3-C7 alkyl chain forming a 4- to 8-membered ring structure together with the nitrogen located between $R_4$ and $R_5$, wherein one or more carbon atoms in the optional $R_4$-$R_5$ ring structure is/are optionally replaced by (a) heteroatom(s) selected from the group consisting of nitrogen (N), oxygen (O) or sulphur (S).

The terms "alkyl" and "alkanediyl" as used herein means straight, branched or cyclic hydrocarbons having a typical meaning, preferably of 1 to 12 carbon atoms, preferably 1 to 8 carbon atoms and more preferably 1 to 6 carbon atoms.

The term "aryl(ene)" as used herein means aromatic hydrocarbons having a typical meaning, preferably of 3 to 12 carbon atoms, preferably single or condensed six-membered rings, more preferably phenyl.

The terms "alkylaryl(ene)" and "arylalkanediyl" as used herein means that the aforementioned aryl(ene) moieties are incorporated into the aforementioned straight or branched alkyl or alkanediyl moieties either at one of the proximal or distal ends of the alkyl or alkanediyl chain or between the alkyl or alkanediyl chains. For example, for $R_1$, proximal end means adjacent to the nitrogen atom of the benzimidazole ring of compound of formula II, while distal means the terminal carbon of the alkyl or aryl moiety which is furthermost from said nitrogen atom. For $R_2$ proximal end means adjacent to —$CY_1$— of the —$CY_1$—$Y_2$— ester group of compound of formula II, while distal means the terminal carbon of the alkyl or alkanediyl moiety which is furthermost from said —$CY_1$— moiety.

The bis-(2-chloroethyl)amino-group located at the benzimidazole ring structure of compound of formula I can be located at any one of positions 4, 5, 6 or 7 of the benzimidazole ring structure. Preferably, the bis-(2-chloroethyl)amino-group is located at the 5 position of the benzimidazole ring structure, as exemplarily illustrated below for compound of formula I:

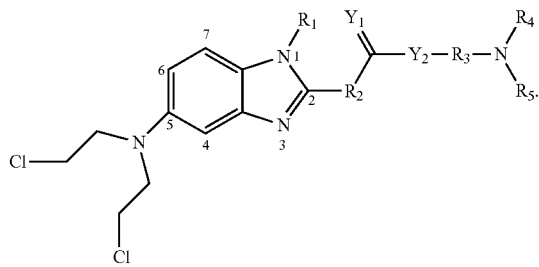

The optional ring structure formed by $R_4$ and $R_5$ neither comprises a C—C double bond representing an integral part of the ring structure, nor are the carbon atoms adjacent to the nitrogen located between $R_4$ and $R_5$ substituted with an oxygen (=O) forming a carbonyl moiety with the respective carbon atom. In particular, the ring structure optionally formed by $R_4$ and $R_5$ together with the nitrogen located between $R_4$ and $R_5$ does not represent a maleimido or a 2,5-dioxopyrrolidine moiety.

(2) The compound according to item (1), wherein $R_1$ is C1-C6 alkyl, $R_2$ and $R_3$ independently from each other represent C1-C6 alkanediyl, $Y_1$ and $Y_2$ represent oxygen, and $R_4$ and $R_5$ independently from each other represent C1-C4 alkyl, preferably $R_1$ is C1-C4 alkyl, $R_2$ and $R_3$ independently from each other represent C1-C4 alkanediyl, $Y_1$ and $Y_2$ represent oxygen, and $R_4$ and $R_5$ independently from each other represent C1-C4 alkyl or form a 5- to 7-membered ring structure together with the nitrogen located between $R_4$ and $R_5$.

(3) The compound according to any one of the preceding items, wherein $R_1$ is C1-C3 alkyl, $R_2$ and $R_3$ independently from each other represent C1-C3 alkanediyl, $Y_1$ and $Y_2$ represent oxygen, and $R_4$ and $R_5$ are the same and represent C1-C3 alkyl or $R_4$ and $R_5$ form a 5- to 7-membered ring structure together with the nitrogen located between $R_4$ and $R_5$.

(4) The compound according to any one of the preceding items, wherein in the ring structure formed by $R_4$ and $R_5$ together with the nitrogen located between $R_4$ and $R_5$, one carbon atom is replaced by one nitrogen atom or one oxygen atom, preferably one oxygen atom.

(5) The compound according to item (4), wherein in the ring structure formed by $R_4$ and $R_5$, a further nitrogen atom is substituted (—$NR_6$—) or unsubstituted (—NH—), preferably substituted with $R_6$ selected from the group consisting of alkyl, aryl, alkylaryl or arylalkyl, more preferably with alkyl.

As to the meaning of the terms "alkyl", "aryl", "alkylaryl" or "arylalkyl", reference is made to the explanations under item (1) above.

(6) The compound according to any one of the preceding items, wherein the ring structure formed by $R_4$ and $R_5$ together with the nitrogen located between $R_4$ and $R_5$ is in the form of a 5- or 6-membered ring, preferably a 6-membered ring.

(7) The compound according to any one of the preceding items, wherein the ring structure formed by $R_4$ and $R_5$ together with the nitrogen located between $R_4$ and $R_5$ is selected from the group consisting of pyrrolidine, piperidine, piperazine and morpholino, preferably piperazine or morpholino, more preferably morpholino.

(8) The compound according to any one of the preceding items, wherein the atoms of the ring structure formed by $R_4$ and $R_5$ together with the nitrogen located between $R_4$ and $R_5$ may be unsubstituted, or substituted with a substituent selected from the group consisting of C1-C4 alkyl, C1-C4 alkoxy, C1-C4 alkylsulfide, unsubstituted amino (—$NH_2$), dialkylamino in which alkyl is C1-C4 alkyl; preferably C1-C4 alkyl or C1-C4 alkoxy; more preferably the ring structure is unsubstituted.

(9) The compound according to any one of the preceding items, wherein $R_1$ is methyl, $R_2$ is propanediyl, $R_3$ is ethanediyl, $Y_1$ and $Y_2$ represent oxygen, and $R_4$ and $R_5$ form a morpholino moiety together with the nitrogen located between $R_4$ and $R_5$.

The compound defined in item (9) has the structural formula

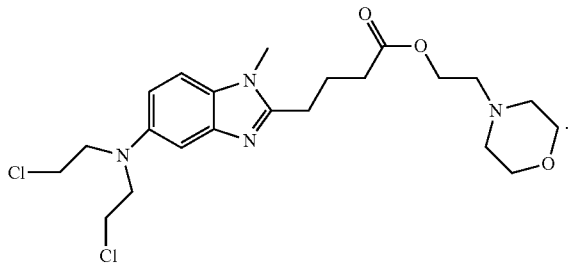 [SMILES: Cn1c(CCCC(=O)OCCN2CCOCC2)nc2cc(N(CCCl)CCCl)ccc21]

(10) The compound according to any one of the preceding items for use in a therapeutic treatment of humans and animals.

(11) A compound of formula II

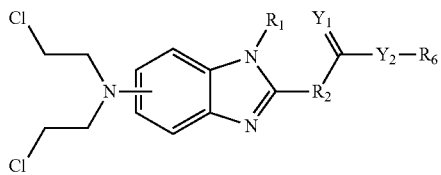

or a pharmaceutically acceptable salt thereof,
wherein $R_1$ and $R_6$ independently from each other represent alkyl, aryl or alkylaryl; $R_2$ is alkanediyl, arylene, alkylarylene or arylalkanediyl; $Y_1$ and $Y_2$ independently from each other represent oxygen or sulphur,
for use in a therapeutic treatment of humans or animals, wherein compound of formula II is used in the form of a pharmaceutical composition, with the proviso that a pharmaceutical composition is excluded that contains either a pharmaceutically acceptable non-ionic surfactant(s) selected from the group consisting of polyethoxylated castor oil or derivatives thereof, block copolymer of ethylene oxide and propylene oxide, or pharmaceutically acceptable saccharide(s) selected from the group consisting of monosaccharide(s), disaccharide(s), oligosaccharide(s), cyclic oligosaccharide(s), polysaccharide(s) and saccharide alcohol (s) which saccharide(s) are contained in the pharmaceutical composition in a ratio by weight of compound of formula II to the saccharide excipient(s) within a range of 1:1 to 5:1.

As to the meaning of the terms "alkyl", "alkanediyl", "aryl (ene)", "alkylaryl(ene)" and "arylalkanediyl", reference is made to the explanations under item (1) above.

As regards the position of the bis(2-chloroethyl)amino-group located at the benzimidazole ring structure, for compound of formula II, analogous substitution patterns apply as explained under item (1) above for compound of formula I.

(12) The compound according to item (11), wherein $R_1$ and $R_6$ independently from each other represent C1-C6 alkyl, $R_2$ is C1-C6 alkanediyl, and $Y_1$ and $Y_2$ represent oxygen; preferably $R_1$ and $R_6$ independently from each other represent C1-C4 alkyl, $R_2$ is C1-C4 alkanediyl, and $Y_1$ and $Y_2$ represent oxygen.

(13) The compound according to item (11) or (12), wherein $R_1$ and $R_6$ independently from each other represent C1-C3 alkyl, $R_2$ is C1-C3 alkanediyl, and $Y_1$ and $Y_2$ represent oxygen.

(14) The compound according to any one of items (11) to (13), wherein $R_1$ and $R_6$ is methyl, $R_2$ is propanediyl, and $Y_1$ and $Y_2$ represent oxygen.

(15) The compound according to any one of the preceding items, wherein compound of formula I or II is in the form of an acid addition salt in which the acid is selected from the group consisting of hydrochloric acid, hydrobromic acid, sulfuric acid, phosphoric acid, glutamic acid, (+)-L-tartaric acid, citric acid, (−)-L-malic acid, DL-lactic acid, L-ascorbic acid, succinic acid, adipic acid, acetic acid, stearic acid, carbonic acid, thiocyanic acid, glycerol-phosphoric acid, L-aspartic acid, maleic acid, fumaric acid, galactaric acid, D-glucuronic acid, glycolic acid, D-glucoheptonic acid, hippuric acid, D-gluconic acid, glutaric acid, sebacic acid, capric (decanoic) acid, lauric acid, palmitic acid, alginic acid, benzoic acid, nicotinic acid, propionic acid, caprylic (octanoic) acid, naphthalene-I,5-disulfonic acid, ethane-I,2-disulfonic acid, cyclamic acid, p-toluenesulfonic acid, methanesulfonic acid, dodecylsulfuric acid, naphthalene-2-sulfonic acid, benzenesulfonic acid, oxalic acid, 2-hydroxy ethanesulfonic acid, ethanesulfonic acid, pannoic (embonic) acid, 2-oxoglutaric acid, 1-hydroxy-2-naphthoic acid, malonic acid, gentisic acid, lactobionic acid, (−)-L-pyroglutamic acid, oleic acid, (+)-camphoric acid, isobutyric acid and orotic acid.

(16) The compound according to any one of the preceding items for use in the therapeutic treatment of diseases selected from the group consisting of acute T cell leukaemia, Erythroleukemia, Ewing osteosarcoma, (hormone dependent) mamma carcinoma, cervix carcinoma, colorectal cancer, medulloblastoma, glioblastoma and astrocytoma, malignant melanoma, histocytic lymphoma, pancreatic carcinoma, prostate cancer (metastasis of a subclavicular lymph node), large cell bronchial carcinoma, colorectal adenocarcinoma, and osteosarcoma; preferably, the disease is selected from the group consisting of acute T cell leukaemia, Erythroleukemia, Ewing osteosarcoma, malignant melanoma, histocytic lymphoma, pancreatic carcinoma, prostate cancer (metastasis of a subclavicular lymph node), large cell bronchial carcinoma, colorectal adenocarcinoma, and osteosarcoma; more preferably, the disease is selected from the group consisting of Ewing osteosarcoma, malignant melanoma, pancreatic carcinoma, prostate cancer (metastasis of a subclavicular lymph node), colorectal adenocarcinoma, and osteosarcoma.

(17) A pharmaceutical composition comprising the compound of formula I and/or the compound of formula II according to any one of the preceding items as a pharmaceutically active agent and at least one pharmaceutically acceptable excipient.

The term "pharmaceutically active agent" as used herein means any active pharmaceutical ingredient intended for treatment or prophylaxis of a disease of a subject to be treated, specifically a mammal such as humans. In general it means any active pharmaceutical ingredient that has an effect on the physiological conditions of the subject.

The term "pharmaceutically acceptable excipient" as used herein means any physiologically harmless or inert, pharmacologically inactive material compatible with the physical and chemical characteristics of the active agent. Suitable pharmaceutically acceptable excipients are generally known in the art.

(18) The pharmaceutical composition according to item (17) for oral and/or parenteral administration.

(19) The pharmaceutical composition according to item (17) or (18), wherein the pharmaceutical composition is free of non-ionic surfactant(s) selected from the group consisting of polyethoxylated castor oil or derivatives thereof, block copolymer of ethylene oxide and propylene oxide and free of saccharide(s) selected from the group consisting of monosaccharide(s), disaccharide(s), oligosaccharide(s), cyclic oligosaccharide(s), polysaccharide(s) and saccharide alcohol(s).

DETAILED DESCRIPTION OF THE INVENTION

The present invention is now described in more detail by referring to further preferred and further advantageous embodiments and examples, which are however presented for illustrative purposes only and shall not be understood as limiting the scope of the present invention.

Conventionally, bendamustine marketed in the form of the free acid, typically in form of its hydrochloride, has the drawback that it is limited to administration by means of intravenous infusion. Furthermore, bendamustine in such conventional form readily decomposes in the presence of water, since bendamustine represents an alkylating agent (also called "alkyl-lost" or "N-lost") due to its $N(CH_2-CH_2-Cl)_2$ moiety.

According to one aspect of the present invention, a compound of formula I

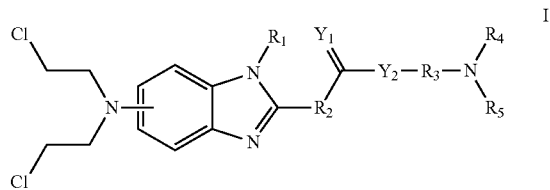

or a pharmaceutically acceptable salt thereof is provided, wherein $R_1$ is alkyl, aryl or alkylaryl; $R_2$ and $R_3$ independently from each other represent alkanediyl, arylene, alkylarylene or arylalkanediyl; $Y_1$ and $Y_2$ independently from each other represent oxygen or sulphur; and $R_4$ and $R_5$ independently from each other represent substituted or unsubstituted alkyl; optionally, $R_4$ and $R_5$ together represent a C3-C7 alkyl chain forming a 4- to 8-membered ring structure together with the nitrogen located between $R_4$ and $R_5$, wherein one or more carbon atoms in the ring structure is/are optionally replaced by (a) heteroatom(s) selected from the group consisting of nitrogen (N), oxygen (O) or sulphur (S).

It was surprisingly found by the present invention that compounds of formula I exhibit a significantly improved antiproliferative efficiency compared to bendamustine HCl conventionally used as active ingredient. Without wishing to be bound by theory, it is believed that the ester compounds of formula I provide for an improved cellular uptake compared with bendamustine in form of the free acid and its salt form owing to an improved combination of solubility in aqueous medium and increased membrane mobility compared with bendamustine (HCl).

According to a preferred a embodiment, compound of formula I may be advantageously structurally modified by structural modifications (i) to (iii), respectively alone or in combination:
(i) $R_1$ is C1-C6 alkyl, $R_2$ and $R_3$ independently from each other represent C1-C6 alkanediyl, $Y_1$ and $Y_2$ represent oxygen, and $R_4$ and $R_5$ independently from each other represent C1-C4 alkyl, preferably $R_1$ is C1-C4 alkyl, $R_2$ and $R_3$ independently from each other represent C1-C4 alkanediyl, $Y_1$ and $Y_2$ represent oxygen, and $R_4$ and $R_5$ independently from each other represent C1-C4 alkyl or form a 5- to 7-membered ring structure together with the nitrogen located between $R_4$ and $R_5$;
(ii) $R_1$ is C1-C3 alkyl, $R_2$ and $R_3$ independently from each other represent C1-C3 alkanediyl, $Y_1$ and $Y_2$ represent oxygen, and $R_4$ and $R_5$ are the same and represent C1-C3 alkyl or $R_4$ and $R_5$ form a 5- to 7-membered ring structure together with the nitrogen located between $R_4$ and $R_5$: and
(iii) $R_1$ is methyl, $R_2$ is propanediyl, $R_3$ is ethanediyl, $Y_1$ and $Y_2$ represent oxygen, and $R_4$ and $R_5$ form a morpholino moiety together with the nitrogen located between $R_4$ and $R_5$.

In this way, particularly suitable selections are determined for substituents $R_1$ to $R_5$, $Y_1$ and $Y_2$.

According to a further preferred embodiment, the ring structure formed by $R_4$ and $R_5$ together with the nitrogen located between $R_4$ and $R_5$ has at least one of the following structural characteristics (a) to (e), respectively alone or in combination:
(a) one carbon atom is replaced by one nitrogen atom or one oxygen atom, preferably one oxygen atom;
(b) a further nitrogen atom is substituted ($-NR_6-$) or unsubstituted ($-NH-$), preferably substituted with $R_6$ selected from the group consisting of alkyl, aryl, alkylaryl or arylalkyl, more preferably with alkyl;
(c) the ring structure is in the form of a 5- or 6-membered ring, preferably a 6-membered ring;
(d) the ring structure is selected from the group consisting of pyrrolidine, piperidine, piperazine and morpholino, preferably piperazine or morpholino, more preferably morpholino;
(e) the atoms of the ring structure may be unsubstituted, or substituted with a substituent selected from the group consisting of C1-C4 alkyl, C1-C4 alkoxy, C1-C4 alkylsulfide, unsubstituted amino ($-NH_2$), dialkylamino in which alkyl is C1-C4 alkyl; preferably C1-C4 alkyl or C1-C4 alkoxy; more preferably the ring structure is unsubstituted.

Structural modifications (a) to (e) provide for particularly advantageous modifications in terms of solubility in aqueous solution and efficacy in terms of cytotoxicity and/or cytostaticity.

According to another preferred aspect of the present invention, a therapeutic treatment comprises administering to the human or animal a therapeutically effective amount of a compound of formula II

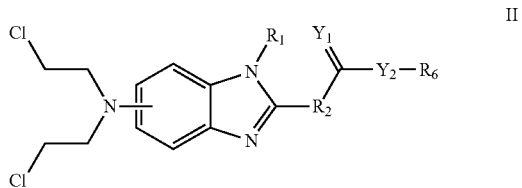

or a pharmaceutically acceptable salt thereof is provided, wherein $R_1$ and $R_6$ independently from each other represent alkyl, aryl or alkylaryl; $R_2$ is alkanediyl, arylene, alkylarylene or arylalkanediyl; $Y_1$ and $Y_2$ independently from each other represent oxygen or sulphur,
wherein compound of formula II is used in the form of a pharmaceutical composition, with the proviso that a pharmaceutical composition is excluded that contains either a pharmaceutically acceptable non-ionic surfactant(s) selected from the group consisting of polyethoxylated castor oil or derivatives thereof, block copolymer of ethylene oxide and propylene oxide, or pharmaceutically acceptable saccharide(s) selected from the group consisting of monosaccharide(s), disaccharide(s), oligosaccharide(s), cyclic oligosaccharide(s), polysaccharide(s) and saccharide alcohol(s) which saccharide(s) are contained in the pharmaceutical composition in a ratio by weight of compound of formula II to the saccharide excipient(s) within a range of 1:1 to 5:1.

It was surprisingly found by the present invention that compounds of formula II exhibit a significantly improved antiproliferative efficiency compared to conventional bendamustine. Without whishing to be bound to theory, it is believed that the ester compounds of formula II provide for an improved cellular uptake compared with bendamustine in form of the free acid owing to an improved combination of solubility in aqueous medium and increased membrane mobility compared with bendamustine (HCl). Hence, compounds of formula II represent valuable active pharmaceutical ingredients providing for parenteral and/or oral uptake. In particular, compounds of formula II render possible to dispense with non-ionic surfactant(s) selected from the group consisting of polyethoxylated castor oil or derivatives thereof, block copolymer of ethylene oxide and propylene oxide, monosaccharide(s), disaccharide(s), oligosaccharide(s), cyclic oligosaccharide(s), polysaccharide(s) and saccharide alcohol(s).

According to a preferred a embodiment, compound of formula II may be advantageously structurally modified by structural modifications (A) to (C), respectively alone or in combination:

(A) $R_1$ and $R_6$ independently from each other represent C1-C6 alkyl, $R_2$ is C1-C6 alkanediyl, and $Y_1$ and $Y_2$ represent oxygen; preferably $R_1$ and $R_6$ independently from each other represent C1-C4 alkyl, $R_2$ is C1-C4 alkanediyl, and $Y_1$ and $Y_2$ represent oxygen;

(B) $R_1$ and $R_6$ independently from each other represent C1-C3 alkyl, $R_2$ is C1-C3 alkanediyl, and $Y_1$ and $Y_2$ represent oxygen; and (C) $R_1$ and $R_6$ is methyl, $R_2$ is propanediyl, and $Y_1$ and $Y_2$ represent oxygen.

Thereby, particularly suitable selections are determined for substituents $R_1$, $R_2$, $R_6$, $Y_1$ and $Y_2$. Surprisingly, already the structurally very simple methyl ester defined under item (III) provides for significantly improved cytotoxicity and/or cytostaticity compared with bendamustine in form of the free acid or its pharmaceutical salt.

According to particular embodiments of the present invention, the compounds of formulae (I) and (II) may be used as a medicament for the therapeutic treatment of diseases selected from the group consisting of acute T cell leukaemia (Jurkat, TI B-152), Erythroleukemia (HEL 92.1.7, TIB-180), Ewing osteosarcoma (SK-ES1, HTB-86), (hormone dependent) mamma carcinoma (MCF-7, HTB-22), cervix carcinoma (multidrug resistant KB-V1), colorectal cancer, medulloblastoma (Daoy, HTB-186), glioblastoma (U-118MG, HTB-15; LN-18, CRL-2610) and astrocytoma (SW1783, HTB-13), malignant melanoma (SK-Mel3, HTB-69), histocytic lymphoma (U-937; CRL-1593.2), pancreatic carcinoma (Capan-1, HTB-80), prostate cancer (metastasis of a subclavicular lymph node) (LnCap clone FGC, CRL-1740), large cell bronchial carcinoma (NCI-H460, HTB-177), colorectal adenocarcinoma (HT-29, HTB-38), osteosarcoma (MG-63, CRL-1427), wherein the terms in brackets after the respective disease denote respectively preferred cancer specifities defined by the cell line and its ATCC-number.

It was surprisingly found by the present invention that compounds of formula I exhibit a significantly improved cytotoxicity and/or cytostaticity compared with bendamustine (hydrochloride) for a large number of different cancer diseases. In particular, this surprisingly improved cytotoxicity and/or cytostaticity could be experimentally demonstrated for representative ester compounds as described in the Examples below, and thus is credible for the analogously modified bendamustine esters of formula I and II.

According to a further preferred embodiment, a pharmaceutical composition is provided which comprises the compound of formula I and/or compound of formula II as a pharmaceutically active agent and at least one pharmaceutically acceptable excipient. In this way, a particularly advantageous pharmaceutical composition is provided which has an improved shelf-life, since compound of formula I has no free carboxylic acid moiety which may react with and/or negatively affect other components of the composition due to its acidity, and furthermore, compound of formula I as such has an improved shelf-life compared to bendamustine (hydrochloride) in the form of the free acid.

The pharmaceutical composition suitably comprises the compound of formula I and/or compound of formula II in a therapeutically effective amount when administered to a human or an animal, for example an amount of at least 0.001 wt-%, preferably at least 0.1 wt-% and more preferably at least 1 wt-%, respectively relative to the total weight of the pharmaceutical composition. Amounts used in conventional therapeutic treatments using conventional bendamustine may provide further useful guidance.

Preferably, suitable pharmaceutically acceptable excipient(s) is/are selected from the group consisting of binders, disintegrants, bulk polymers, glidants, lubricants and preservatives, without being limited thereto.

The term "binder" as used herein means a binding agent which improves adhesion in between particles of the pharmaceutically active agent.

The term "disintegrant" as used herein means an agent providing for rapid disintegration of a pharmaceutical composition into smaller fragments when in contact with water, wherein dissolution of the pharmaceutical composition and in particular of a pharmaceutically active agent comprised therein is improved.

The term "bulk polymer" as used herein means a polymeric filling agent which is typically added to a pharmaceutical composition in suitable amounts.

The term "glidants and lubricants" as used herein means components acting as formulation and processing aids.

The term "preservatives" as used herein means a substance or mixture of substances which prevents decomposition of a pharmaceutical composition, e.g. microbial or bacterial decomposition.

According to a preferred embodiment, the pharmaceutical composition is free of non-ionic surfactant(s) selected from the group consisting of polyethoxylated castor oil or derivatives thereof, block copolymer of ethylene oxide and propylene oxide, and free of saccharide(s) selected from the group consisting of monosaccharide(s), disaccharide(s), oligosaccharide(s), cyclic oligosaccharide(s), polysaccharide(s) and saccharide alcohol(s).

In this way, owing to the specific selection of compounds of formula I and II as the active pharmaceutical ingredient, it can be advantageously dispensed with the use of the above-defined non-ionic surfactant(s) and saccharide(s) as pharmaceutically acceptable excipients.

The following examples further illustrate the invention. They are provided for illustrative purposes only and are not intended to limit the invention in any way. The examples and modifications or other equivalents thereof will become apparent to those versed in the art in the light of the present entire disclosure.

EXAMPLES

Analytic Methods

HPLC/MS
Test solution: (c=1 mg/ml), solvent: acetonitrile/methanol=8/2 (v/v).
Column: Merck LiChrospher 100 DIOL, 5 µm, (250×4.0) mm
Mobile phase A: acetonitrile/methanol=9/1 (v/v)+0.5 g/L ammonium acetate+1.4 mL/L acetic acid.
Mobile phase B: acetonitrile/methanol=6/4 (v/v)+0.5 g/L ammonium acetate+1.4 mL/L acetic acid.
Gradient: 0 min 100% A; 10 min 100% A; 15 min 10% A; 18 min 10% A; 20 min 100% A; 25 min 100% A.
Injection: 10 µL
Flow rate: 1.3 mL/min
UV-Detection: 254 nm
Mass spectrometric method: ESI+
NMR
Bruker Avance, 500 MHz, Temperature 295 K

Example 1

Preparation of Compounds of Formula I a) Bendamustine morpholinoethylester

Bendamustine morpholinoethylester (alternative denotation: bendamustine mofetylester or, according to IUPAC-nomenclature 2-morpholinoethyl 4-(5-(bis(2-chloroethyl) amino)-1-methyl-1H-benzo[d]imidazol-2-yl)butanoate) having the structural formula

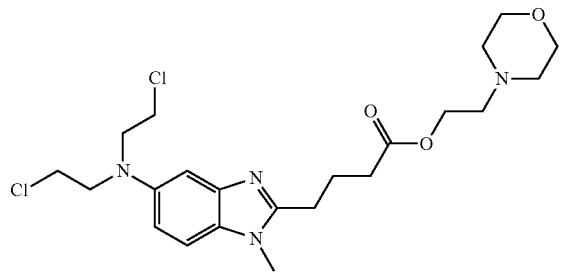 [SMILES: Cn1c(CCCC(=O)OCCN2CCOCC2)nc2cc(N(CCCl)CCCl)ccc21]

was prepared as follows:

Bendamustine free base (1.0 g, 2.79 mmol) in dichloromethane (90 ml), morpholinoethanol (0.44 ml, 3.35 mmol) and DMAP (20 mg) were added with stirring. A solution of N,N'-Dicyclohexylcarbodiimide (0.63 g, 3.05 mmol) in dichloromethane (90 ml) was added dropwise over 50 min. After 15 min, a clear reaction solution was obtained and after 70 min a precipitate of dicyclohexyl urea occurred. The reaction mixture was stirred at ambient temperature for a total time of 24 h. After concentration to half of the volume and cooling to 0° C., the precipitate was removed by filtration. Then the solution was extracted with diluted HCl (1 ml 37% HCl to 60 ml Water, 30 ml+2×15 ml portions). The aqueous phase was treated with 25% $NH_3$ (1.6 ml, pH 7-8) and extracted with dichloromethane (20+2×10 ml). Evaporation of the combined organic solvents resulted in a crude oil (1.38 g) that was purified via column chromatography (40 g silica, 10% MeOH/dichloromethane) to afford a slightly yellowish oil (1.26 g) that crystallized after seeding. Further drying in vacuum resulted in 1.08 g (82%) of product as slightly yellowish crystals.

$^1$H NMR (500 MHz, DMSO-$d_6$, ppm): δ=7.33 (d, 8.8 Hz, 1H, H6), 6.93 (d, 2.2 Hz, 1H, H4), 6.79 (dd, 2.2 Hz, 8.8 Hz, 1H, H7), 4.12 (t, 5.9 Hz, 2H, O—C$\underline{H}_2$—CH$_2$-Morpholino), 3.71 (m (apparent singlet), 8H, N—C$\underline{H}_2$—C$\underline{H}_2$—Cl), 3.67 (s, 3H, CH$_3$), 3.54 (m, 4H, N(—CH$_2$—C$\underline{H}_2$—)$_2$O), 2.85 (t, 7.3 Hz, 2H, COOR—CH$_2$—CH$_2$—C$\underline{H}_2$), 2.51 (t, 6 Hz, 2H, O—CH$_2$—C$\underline{H}_2$-Morpholino, interfering with DMSO solvent signal), 2.48 (t, 7.3 Hz, 2H, COOR—C$\underline{H}_2$—CH$_2$—(CH$_2$), 2.40 (m, 4H, N(—C$\underline{H}_2$—CH$_2$—)$_2$O), 2.02 (pent, 7.3 Hz, 2H, CO$_2$R—CH$_2$—C$\underline{H}_2$—(CH$_2$).

$^{13}$C-{H}-NMR (126 MHz, DMSO-$d_6$, ppm): δ=172.5 ($C^{15}$OOR), 154.3 ($C^2$), 143.4 ($C^6$), 142.1 ($C^4$), 129.2 ($C^9$), 110.0 ($C^8$), 109.8 ($C^7$), 102.2 ($C^5$), 66.0 ($C^{19,20}$), 60.8 ($C^{16}$), 56.4 ($C^{17}$), 53.4 ($C^{10,10'}$), 53.3 ($C^{18,21}$), 41.3 ($C^{11,11'}$), 32.8 ($C^{14}$), 29.3 ($C^{23}$), 25.5 ($C^{12}$), 22.0 ($C^{13}$).

LC-MS (ESI$^+$): m/z=471.1 (M+H$^+$);
HPLC: peak at retention time 2.26 min.
IR (KBr) wavenumber=2939 (m, C—H), 1734 (s, C=O), 1628 (m), 1589 (m), 1497 (s), 1458 (m), 1443 (m), 1408 (w), 1384 (m), 1346 (m), 1322 (m), 1277 (m), 1169 (s), 1117 (s), 1070 (w), 1036 (w), 1010 (m), 988 (w), 916 (w), 866 (m), 830 (m), 788 (m), 731 (w), 658 (w), 521 (w).
IR (solution in CHCl$_3$): wavenumber=3009 (m), 2965 (s, CH), 2865 (m), 1730 (s, C=O), 1629 (m), 1591 (m), 1496 (s), 1456 (m), 1405 (m), 1387 (w), 1353 (m), 1302 (m), 1250 (m), 1151 (s), 1117 (s), 1068 (w), 1013 (w), 915 (w), 859 (w).
melting point: 82-82.7° C. determined with Büchi melting point apparatus.
Powder X-ray diffraction (XRD) data:

| 2Θ | [°] | 7.48 | 11.24 | 12.27 | 13.15 | 13.69 | 14.03 | 14.31 | 15.02 | 15.99 |
|---|---|---|---|---|---|---|---|---|---|---|
| d | [Å$^{-1}$] | 11.80 | 7.87 | 7.21 | 6.73 | 6.46 | 6.31 | 6.18 | 5.89 | 5.54 |
| FWHM | [°] | | 0.16 | 0.16 | | | | | 0.17 | |
| | | 17.21 | 17.58 | 18.80 | 18.94 | 19.43 | 19.57 | 20.05 | 20.25 | 20.45 |
| | | 5.15 | 5.04 | 4.72 | 4.68 | 4.57 | 4.53 | 4.43 | 4.38 | 4.34 |
| | | 0.15 | | | | | | | | |
| | | 21.81 | 22.61 | 22.86 | 23.17 | 23.40 | 24.59 | 24.71 | 25.05 | 25.39 |
| | | 4.07 | 3.93 | 3.89 | 3.84 | 3.80 | 3.62 | 3.60 | 3.55 | 3.51 |
| | | 0.22 | | | | | | | | |
| | | 27.94 | 28.83 | 29.53 | 30.01 | 30.39 | 31.59 | 31.73 | 32.57 | 32.96 |
| | | 3.19 | 3.09 | 3.02 | 2.98 | 2.94 | 2.83 | 2.82 | 2.75 | 2.72 |
| | | | | 0.16 | 0.19 | 0.12 | | | | |
| | | 35.36 | 36.36 | 36.99 | 40.78 | 41.88 | 44.30 | 44.93 | 45.24 | 46.17 |
| | | 2.54 | 2.47 | 2.43 | 2.21 | 2.16 | 2.04 | 2.02 | 2.00 | 1.96 |
| | | | | | 0.17 | | | | | |

FWHM = full width at half maximum b) Bendamustine Morpholinoethyl Ester Hydrochloride Bendamustine morpholinoethyl ester (120 mg, 0.25 mmol) was dissolved in ethyl acetate (8 ml). HCl gas was bubbled through this solution. The product precipitated as colourless flakes (hydrochloride precipitation from dichloromethane failed) and was isolated by filtration, washed with ethyl acetate and dried in vacuo to yield a colourless hygroscopic solid (110 mg, 81%), which rapidly turned into a paste-like substance upon exposure to air.

$^1$H NMR (500 MHz, DMSO-$d_6$, ppm): δ=14.98 (s, 1H, Ar—NH$^+$), 11.82 (s, 1H, NH$^+$ morpholino), 7.73 (d, 9.2 Hz, 1H, H6), 7.13 (dd, 2.2 Hz, 9.2 Hz, 1H, H7), 6.92 (d, 2.2 Hz, 1H, H4), 4.55 (t, 5.9 Hz, 2H, O—C$\underline{H}_2$—CH$_2$-Morpholino), 3.91 (m, 7H, CH$_3$, N(—CH$_2$—C$\underline{H}_2$—)$_2$O), 3.83 (t, 6.5 Hz, 4H, CH$_2$Cl), 3.77 (t, 6.5 Hz, 4H, NC$\underline{H}_2$CH$_2$Cl) 3.40 (m, 4H, N(—C$\underline{H}_2$—CH$_2$—)$_2$O), 3.20 (t, 7.3 Hz, 2H, COOR—CH$_2$—CH$_2$—C$\underline{H}_2$), 3.12 (m, br, 2H O—CH$_2$—C$\underline{H}_2$— Morpholino), 2.58 (t, 7.3 Hz, 2H, COOR—C$\underline{H}_2$—CH$_2$—(CH$_2$), 2.09 (pent, 7.3 Hz, 2H, COOR—CH$_2$—C$\underline{H}_2$—(CH$_2$).

LC-MS (ESI$^+$): m/z=471.1 (M+H$^+$).

HPLC: peak at retention time 2.23 min.

c) Bendamustine Piperidinoethylester

Bendamustine piperidinoethylester (IUPAC-nomenclature: 2-(piperidin-1-yl)ethyl 4-(5-(bis(2-chloroethyl)amino)-1-methyl-1H-benzo[d]imidazol-2-yl)butanoate) having the structural formula

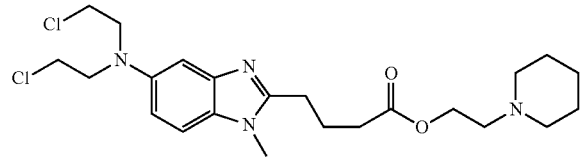 [SMILES: Cn1c(CCCC(=O)OCCN2CCCCC2)nc2cc(N(CCCl)CCCl)ccc21]

was synthesized analogous to Example 1a), wherein the substrates where applied in the following amounts:
bendamustine base (1.0 g, 2.79 mmol), piperidinoethanol (430 mg, 3.35 mmol), DMAP (20 mg), N,N'-Dicyclohexylcarbodiimide (0.66 g, 3.51 mmol).

Yield: 610 mg (1.30 mmol, 46.6%) of a yellow oil.

$^1$H NMR (500 MHz, DMSO-$d_6$, ppm): δ=7.33 (d, 8.8 Hz, 1H, H$^8$), 6.93 (d, 2.2 Hz, 1H, H$^5$), 6.79 (dd, 2.2 Hz, 8.8 Hz, 1H, H$^7$), 4.10 (t, 5.9 Hz, 2H, O—C$^{16}\underline{H}_2$), 3.71 (m (apparent singlet), 8H, N—C$\underline{H}_2$—C$\underline{H}_2$—Cl), 3.66 (s, 3H, CH$_3$), 2.85 (t, 7.3 Hz, 2H, C$^{12}\underline{H}_2$), 2.51 (t, br., 6 Hz, 2H, C$^{17}\underline{H}_2$-piperidine+DMSO), 2.46 (t, 7.3 Hz, 2H, COOR—C$^{14}\underline{H}_2$), 2.39 (br, 4H, C$^{18,22}\underline{H}_2$), 2.02 (pent, 7.3 Hz, 2H, COOR—CH$_2$—C$\underline{H}_2$—CH$_2$), 1.45 (m, 4H, C$^{19,21}\underline{H}_2$), 1.35 (m, 2H, C$^{20}\underline{H}_2$).

$^{13}$C-{H}-NMR (126 MHz, DMSO-$d_6$, ppm): δ=173 ($\underline{C}$OOR), 154 (C$^2$), 143 (C$^6$), 142 (C$^4$), 129 (C$^9$), 110.1 (C$^8$), 109.9 (C$^7$), 102 (C$^5$), 61 (C$^{16}$), 57 (C$^{17}$), 54 (C$^{18,22}$), 53.5 (C$^{10,10'}$), 41 (C$^{11,11'}$), 33 (C$^{14}$), 29 (C$^{23}$, CH$_3$), 25.6 (C$^{12}$), 25.5 (C$^{19,21}$), 24 (C$^{20}$), 22 (C$^{13}$).

HPLC-MS: m/z=469 (M+H$^+$).

HPLC: peak at retention time 3.71 min.

IR (solution in CHCl$_3$): wavenumber=2942 (s, CH), 1729 (s, C=O), 1629 (m), 1591 (m), 1496 (s), 1444 (m), 1405 (m), 1387 (w), 1353 (m), 1305 (m), 1251 (m), 1154 (s), 1102 (w), 1041 (w), 1011 (w), 976 (w), 917 (w), 835 (w).

d) Bendamustine Pyrrolidinoethylester

Bendamustine Pyrrolidinoethylester (IUPAC-nomenclature: 2-(pyrrolidin-1-yl)ethyl 4-(5-(bis(2-chloroethyl)amino)-1-methyl-1H-benzo[d]imidazol-2-yl)butanoate) having the structural formula

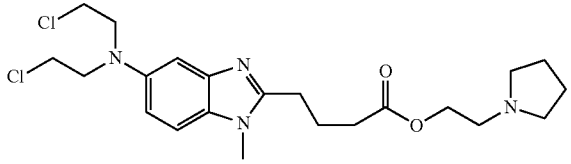 [SMILES: Cn1c(CCCC(=O)OCCN2CCCC2)nc2cc(N(CCCl)CCCl)ccc21]

Synthesis was carried out analogous to Example 1a), wherein the starting materials were applied in following amounts:
bendamustine base (1.0 g, 2.79 mmol), pyrrolidinoethanol (390 mg, 3.51 mmol), DMAP (20 mg), N,N'-Dicyclohexylcarbodiimide (0.66 g, 3.05 mmol).

yield: 590 mg (1.32 mmol, 47.5%) of a slightly yellow oil.

$^1$H NMR (500 MHz, DMSO-$d_6$, ppm): δ=7.33 (d, 8.8 Hz, 1H, H$^8$), 6.93 (d, 2.2 Hz, 1H, H$^5$), 6.79 (dd, 2.2 Hz, 8.8 Hz, 1H, H$^7$), 4.13 (t, 5.9 Hz, 2H, C$^{16}$H), 3.71 (m (apparent singlet), 8H, N—C$\underline{H}_2$—C$\underline{H}_2$—Cl), 3.66 (s, 3H, C$^{23}$H$_3$), 2.84 (t, 7.3 Hz, 2H, C$^{12}\underline{H}_2$), 2.64 (t, 5.9 Hz, 2H, C$^{17}$H2), 2.49 (m, 6H, C$^{14}$H$_2$+C1$^{8,21}$H$_2$), 2.02 (pent, 7.3 Hz, 2H, C$^{13}$H$_2$), 1.66 (m, 4H, C$^{19,20}$H$_2$).

$^{13}$C-{H}-NMR (126 MHz, DMSO-$d_6$, ppm): δ=173 ($\underline{C}$OOR), 155 (C$^2$), 144 (C$^6$), 143 (C$^4$), 129 (C$^9$), 111 (C$^8$), 110 (C$^7$), 103 (C$^5$), 63 (C$^{16}$), 54.2-54.3 (C$^{10,10'}$+C$^{18,22}$), 54 (C$^{17}$), 42 (C$^{11,11'}$), 33 (C$^{14}$), 30 (C$^{23}$, CH$_3$), 26 (C$^{12}$), 24 (C$^{19,20}$), 23 (C$^{13}$).

HPLC-MS: m/z=455 (M+H$^+$)

HPLC: peak at retention time 4.71 min.

IR (solution in CHCl$_3$): wavenumber=2963 (s, CH), 2806 (m), 1729 (s, C=O), 1629 (m), 1591 (m), 1496 (s), 1462 (m), 1405 (m), 1353 (m), 1251 (m), 1153 (s), 1102 (w), 1020 (w), 976 (w), 874 (w), 835 (w).

e) Bendamustine Methylpiperazinoethylester

Bendamustine Methylpiperazinoethylester (IUPAC-nomenclature: 2-(4-methylpiperazin-1-yl)ethyl 4-(5-(bis(2-chloroethyl)amino)-1-methyl-1H-benzo[d]imidazol-2-yl) butanoate) having the structural formula

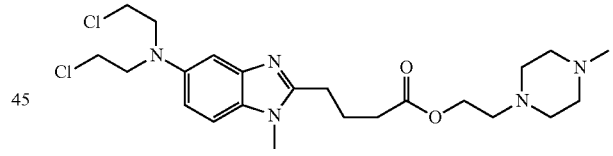

was prepared analogous to Example 1a), wherein the starting materials were applied in the following amounts:
bendamustine base (1.0 g, 2.79 mmol), methylpiperazinoethanol (555 mg, 3.35 mmol), DMAP (20 mg), N,N'-Dicyclohexylcarbodiimide (0.68 g, 3.29 mmol).

Yield: 1.0 g (2.06 mmol, 74.0%) of a slightly yellow oil.

$^1$H NMR (500 MHz, DMSO-$d_6$, ppm): δ=7.33 (d, 8.8 Hz, 1H, H$^8$), 6.93 (d, 2.2 Hz, 1H, H$^5$), 6.79 (dd, 2.2 Hz, 8.8 Hz, 1H, H$^7$), 4.11 (t, 5.9 Hz, 2H, C$^{16}$H), 3.71 (m (apparent singlet), 8H, N—C$\underline{H}_2$—C$\underline{H}_2$—Cl), 3.66 (s, 3H, C$^{23}$H$_3$), 2.84 (t, 7.3 Hz, 2H, C$^{12}$H$_2$), 2.51 (t, 6 Hz, 2H, C$^{17}$H$_2$), 2.47 (t, 7.3 Hz, 2H, C$^{14}$H$_2$), 2.40 (br, 2H, C$^{18,21}$H$_2$), 2.26 (br, 2H, C$^{19,20}$H$_2$), 2.13 (s, 3H, C$^{22}$H$_3$), 2.02 (pent, 7.3 Hz, 2H, C$^{13}$H$_2$).

$^{13}$C-{H}-NMR (126 MHz, DMSO-$d_6$, ppm): δ=173 ($\underline{C}$OOR), 154 (C$^2$), 143 (C$^6$), 142 (C$^4$), 129 (C$^9$), 110.1 (C$^8$), 109.9 (C$^7$), 102 (C$^5$), 61 (C$^{16}$), 56 (C17), 55 (C$^{18,21}$), 54 (C$^{10,10'}$), 53 (C$^{19,20}$), 46 (C$^{22}$H$_3$), 41 (C$^{11,11'}$), 33 (C$^{12}$), 29 (C$^{23}$, CH$_3$), 26 (C$^{12}$), 22 (C$^{13}$).

HPLC-MS: m/z=484 (M+H$^+$).

HPLC: peak at retention time 5.27 min.

IR (solution in CHCl$_3$): wavenumber=2945 (s, CH), 2806 (s), 1729 (s, C=O), 1629 (m), 1592 (m), 1496 (s), 1459 (m), 1405 (m), 1354 (m), 1284 (m), 1234 (m), 1153 (s), 1101 (w), 1013 (w), 835 (w).

Example 2

Preparation of Compounds of Formula II a) Bendamustine Methylester

A 250 mL three-necked round bottom flask equipped with a magnetic stirring bar, internal thermometer and a reflux-condenser with oil ventile was charged with phosphorus oxychloride (101 g, 60.0 mL, 657 mmol) and heated to an internal temperature of about 60-70° C. DHBM (30 g, 89.4 mmol) was added in portions. After the addition was completed the mixture was heated to reflux temperature and stirring was continued for a further 15 min. The mixture was allowed to reach room temperature and 1,2-dimethoxyethane (67.5 mL) was added with stirring (Solution 1). A 1000 mL three-necked round bottom flask was charged with potassium bicarbonate (321.8 g, 3215 mmol) and potable water (394 mL). Solution 1 was added slowly with stirring, maintaining an internal temperature of about 20 to 30° C., after which stirring was continued for a further 60 min. The resulting solid was isolated, washed with water (4×75 mL) and used without further purification. Yield: 71.6 g, moist.

$^1$H NMR (500 MHz, DMSO-d$_6$, ppm): δ=7.32 (d, $^3$J=8.8 Hz, 1H, arom. R$_2$NCCH=C<u>H</u>), 6.93 (d, $^4$J=1.6 Hz, 1H, arom. R$_2$NCCH), 6.79 (dd, $^3$J=8.8 Hz, $^4$J=1.6 Hz, 1H, arom. R$_2$NCC<u>H</u>=CH), 3.71 (s, 8H, C<u>H$_2$</u>C<u>H$_2$</u>Cl), 3.65 (s, 3H, CH$_3$N), 3.60 (s, 3H, CH$_3$O), 2.83 (t, $^3$J=7.4 Hz, 2H, CH$_2$—CH$_2$—C<u>H$_2$</u>-Ester), 2.49 (t, $^3$J=7.3 Hz, 2H, C<u>H$_2$</u>—CH$_2$—CH$_2$-Ester), 2.02 (m, 2H, CH$_2$—C<u>H$_2$</u>—CH$_2$-Ester).

$^{13}$C-{H}-NMR (125.77 MHz, DMSO-d$_6$, ppm): δ=173.6 (COOMe), 154.8 (arom.), 143.8 (arom.), 142.7 (arom.), 129.8 (arom.), 110.6 (arom.), 110.4 (arom.), 102.7 (arom.), 54.0 (2×CH$_2$Cl), 51.7 (OCH$_3$), 41.9 (2×CH$_2$N), 33.1 (CH$_2$), 29.8 (CH$_3$), 26.0 (CH$_2$), 22.5 (CH$_2$).

HPLC: peak at retention time 2.18 min.

b) Bendamustine Ethylester

A 500 mL three-necked round bottom flask equipped with a magnetic stirring bar, internal thermometer and a reflux-condenser with oil ventile was charged with phosphorus oxychloride (134 g, 80.0 mL, 874 mmol) and heated to an internal temperature of about 60-70° C. DHBE (40 g, 114 mmol) was added in portions. After the addition was completed the mixture was heated to reflux temperature and stirring was continued for a further 15 min. The mixture was allowed to reach room temperature and 1,2-dimethoxyethane (90 mL) was added with stirring (Solution 1). A 2000 mL three-necked round bottom flask was charged with potassium bicarbonate (412.1 g, 4115 mmol) and potable water (525 mL). Solution 1 was added slowly with stirring, maintaining an internal temperature of about 20 to 30° C., after which stirring was continued for a further 60 min. The resulting solid was isolated, washed with water (4×100 mL) and used without further purification. (The product may optionally be dried in vacuum at temperatures of not more than 40° C. Yield (moist): 89.26 g; calculated dry: 46.3 g, >100%; (product usually contains residual water even after drying).

$^1$H NMR (600 MHz, DMSO-d$_6$, ppm): δ=7.73 (d, $^3$J=8.8 Hz, 1H, arom. R$_2$NCCH=C<u>H</u>), 6.92 (d, $^4$J=2.3 Hz, 1H, arom. R$_2$NCCH), 6.78 (dd, $^3$J=8.8 Hz, $^4$J=2.3 Hz, 1H, arom. R$_2$NCC<u>H</u>=CH), 4.04 (q, $^3$J=7.1 Hz, 2H, OC<u>H$_2$</u>CH$_3$), 3.70 (s, 8H, CH$_2$CH$_2$Cl), 3.65 (s, 3H, CH$_3$N), 2.92 (t, $^3$J=7.4 Hz, 2H, CH$_2$—CH$_2$—C<u>H$_2$</u>-Ester), 2.44 (t, 3J=7.3 Hz, 2H, C<u>H$_2$</u>—CH$_2$—CH$_2$-Ester), 2.00 (m, 2H, CH$_2$—C<u>H$_2$</u>—CH$_2$-Ester).

$^{13}$C-{H}-NMR (150 MHz, DMSO-d$_6$, ppm): δ=172.7 (COOEt), 154.4 (arom.), 143.4 (arom.), 142.3 (arom.), 129.3 (arom.), 110.2 (arom.), 110.0 (arom.), 102.3 (arom.), 59.8 (<u>C</u>H$_2$CH$_3$), 53.6 (2×CH$_2$Cl), 41.5 (2×CH$_2$N), 32.9 (CH$_2$), 29.4 (CH$_3$), 25.7 (CH$_2$), 22.2 (CH$_2$), 14.2 (CH$_2$<u>C</u>H$_3$).

HPLC: peak at retention time 2.14 min.

LC-MS (ESI$^+$): m/z=386.2 (M+H$^+$; 100% relative Intensity)

c) Bendamustine Propyl Ester

Bendamustine HCl×H$_2$O (1 g) was suspended in propanol (5 mL). Hydrochloric acid (37%, ~0.2 mL) was added and the stirred mixture was heated to reflux temperature for 5 h. After that the product solution was added to potassium bicarbonate (0.6 g) in RO-water (50 mL); final pH value was between 7 and 8. The product precipitated already as a solid, which was isolated by filtration, washed with RO-water (3×1 mL) and dried in the fumehood. The obtained solid was isolated by filtration; yield: 0.85 g.

$^1$H NMR (600 MHz, DMSO-d$_6$, ppm): δ=7.32 (d, $^3$J=8.8 Hz, 1H arom. R$_2$NCCH=C<u>H</u>), 6.92 (d, $^4$J=2.4 Hz, 1H, Arom. R$_2$NCC<u>H</u>), 6.78 (dd, $^3$J=8.8 Hz, $^4$J=2.3 Hz, 1H, Arom. R$_2$NCC<u>H</u>=CH), 3.96 (t, 2H, $^3$J=6.8 Hz, CH$_2$ propyl), 3.70 ("s", 8H, 2×NCH$_2$CH$_2$Cl), 3.65 (s, 3H, CH$_3$N), 2.83 (t, $^3$J=7.4 Hz, 2H, CH$_2$C$_{imidaz}$), 2.46 (t, $^3$J=7.3 Hz, 2H, CH$_2$COO), 2.01 (ft, $^3$J=7.3, 7.4 Hz, 2H, CH$_2$C<u>H$_2$</u>CH$_2$), 1.56 (tq, $^3$J=7.3, 6.8 Hz, CH$_2$), 0.87 (t, $^3$J=7.4, 6.8 Hz, 3H, CH$_3$ propyl).

$^{13}$C-{H}-NMR (150 MHz, MeOH-d$_4$, ppm): δ=172.62 (COO), 154.26 (CN$_2$), 143.20 (C arom.), 142.18 (C arom.), 129.19 (C arom.), 110.07 (CH arom.), 109.84 (CH arom.), 102.16 (CH arom.), 65.20 (CH$_2$ propyl), 53.42 (2×CH$_2$Cl), 41.36 (2×CH$_2$N), 32.75 (CH$_2$COO), 29.31 (CH$_3$N), 25.54 (CH$_2$—C(imidazol)), 22.06 (CH$_2$<u>C</u>H$_2$CH$_2$), 21.45 (CH$_2$<u>C</u>H$_2$CH$_3$ propyl), 10.19 (CH$_3$ propyl).

HPLC: peak at retention time 2.12 min.

LC-MS (ESI$^+$): m/z=400.2 (M+H$^+$; 100% relative Intensity)

d) Bendamustine Isopropyl Ester

Bendamustine HCl×H$_2$O (1 g, 2.83 mmol) was suspended iso-propanol (5 mL). Hydrochloric acid (0.3 mL; 8N in iso-propanol) was added and the stirred mixture was heated to reflux temperature for 5 h. After that the product solution was added to potassium bicarbonate (0.6 g) in RO-water (50 mL); final pH value was between 7 and 8. An oil forms. The emulsion was extracted twice with ethyl acetate (30+20 mL), the combined organic extracts were dried over sodium sulphate and concentrated under reduced pressure with a rotary evaporator (0.9 g, crystalline, crude material). The solid was slurried with methyl-tertiary butyl-ether (5 mL), isolated by filtration, washed with cold methyl-tertiary butyl-ether (2×0.8 mL) and dried in the fumehood. Yield: 0.47 g.

$^1$H NMR (600 MHz, DMSO-d6, ppm): δ=7.32 (d, $^3$J=8.8 Hz, 1H, Arom. R$_2$NCCH=C<u>H</u>), 6.92 (d, $^4$J=2.4 Hz, 1H, Arom. R$_2$NCC<u>H</u>), 6.78 (dd, $^3$J=8.8 Hz, $^4$J=2.3 Hz, 1H, Arom. R$_2$NCC<u>H</u>=CH), 4.88 (hept, 1H, $^3$J=6.3 Hz, CH isopropyl), 3.70 ("s", 8H, 2×NCH$_2$CH$_2$Cl), 3.66 (s, 3H, CH$_3$N), 2.82 (t, $^3$J=7.4 Hz, 2H, CH$_2$C$_{imidaz}$), 2.41 (t, $^3$J=7.3 Hz, 2H, CH$_2$COO), 1.99 (tt, $^3$J=7.3, 7.4 Hz, 2H, CH$_2$C<u>H$_2$</u>CH$_2$), 1.17 (d, $^3$J=6.3 Hz, 6H, CH$_3$ (isopropyl).

$^{13}$C-{H}-NMR (150 MHz, MeOH-d$_4$, ppm): δ=172.18 (COO), 154.41 (CN$_2$), 143.31 (C arom.), 142.33 (C arom.), 129.32 (C arom.), 110.23 (CH arom.), 110.01 (CH arom.), 102.29 (CH arom.), 67.09 (CH isopropyl), 53.57 (2×CH$_2$Cl), 41.50 (2×CH$_2$N), 33.21 (CH$_2$COO), 29.47 (CH$_3$N), 25.68 (CH$_2$), 22.26 (CH$_2$), 21.69 (CH$_3$ isopropyl).

HPLC: peak at retention time 2.12 min.

LC-MS (ESI$^+$): m/z=400.2 (M+H$^+$; 100% relative Intensity)

e) Bendamustine Butyl Ester

Bendamustine HCl×H$_2$O (1 g) was suspended in butanol (5 mL). Hydrochloric acid (aq., 37%, ~0.2 mL) was added and the stirred mixture was heated to reflux temperature for 5 h. After that the product solution was added to potassium bicarbonate (0.6 g) in RO-water (50 mL); final pH value was between 7 and 8. An oil forms. The emulsion was extracted twice with ethyl acetate (30+20 mL), the combined organic extracts were dried over sodium sulphate and concentrated under reduced pressure with a rotary evaporator. The product was obtained as an oil; yield: 0.95 g.

$^1$H NMR (600 MHz, DMSO-d6, ppm): δ=7.32 (d, $^3$J=8.8 Hz, 1H, Arom. R$_2$NCCH=CH), 6.92 (d, $^4$J=2.4 Hz, 1H, Arom. R$_2$NCCH), 6.78 (dd, $^3$J=8.8 Hz, $^4$J=2.3 Hz, 1H, Arom. R$_2$NCCH=CH), 4.00 (t, 2H, $^3$J=6.7 Hz, CH$_2$ butyl), 3.70 ("s", 8H, 2×NCH$_2$CH$_2$Cl), 3.65 (s, 3H, CH$_3$N), 2.83 (t, $^3$J=7.4 Hz, 2H, CH$_2$C$_{imidaz.}$), 2.45 (t, $^3$J=7.3 Hz, 2H, CH$_2$COO), 2.00 (ft, $^3$J=7.3, 7.4 Hz, 2H, CH$_2$CH$_2$CH$_2$), 1.53 (m, CH$_2$(butyl)), 1.30 (m, CH$_2$(butyl)), 0.88 (t, $^3$J=7.4, Hz, 3H, CH$_3$ (butyl)).

$^{13}$C-{H}-NMR (150 MHz, MeOH-d$_4$, ppm): δ=172.74 (COO), 154.37 (CN$_2$), 143.29 (C arom.), 142.34 (C arom.), 129.31 (C arom.), 110.23 (CH arom.), 110.00 (CH arom.), 102.26 (CH arom.), 63.57 (CH$_2$O butyl), 53.57 (2×CH$_2$Cl), 41.49 (2×CH$_2$N), 32.90 (CH$_2$COO), 30.26 (CH$_2$ butyl), 29.45 (CH$_3$N), 25.68 (CH$_2$-imidazol), 22.19 (CH$_2$CH$_2$CH$_2$COO), 18.70 (CH$_2$CH$_3$ butyl), 13.62 (CH$_3$ butyl).

HPLC: peak at retention time 2.11 min.

LC-MS (ESI$^+$): m/z=414.2 (M+H$^+$; 100% relative Intensity)

Example 3

Determination of Cytotoxicity

General Procedure

For the determination of cytotoxicity two different assays were used depending on the characteristics of the treated cells. For adherently growing cells the crystal violet assay[b] was used. Instead of complete removal of the conditioned culture medium, 100 μl of fresh medium, containing a two-fold higher concentration of the test compounds than the desired final concentration were added 2-3 days after seeding the cells at a density of about 5000 cells/well (100 μl).

For loosely adherent cells and cells growing in suspension, the MTT-assay[a] was used. Suspension cells were seeded at a density of 8000 cells/well (100 μl). In case of suspension cells, 100 μl of medium, containing the test compounds bendamustine HCl and bendamustine mofetil ester (or bendamustine methyl ester), were added directly after seeding of the cells. Loosely adherent cells were seeded at a density of 5000 cells/well (100 μl) and treated as described for the crystal violet assay.

In all cases, one plate was measured at the time, when substances were added (t$_0$-plate). The MTT-(2.5 mg/ml) solution (PBS) was freshly prepared for each measurement. 20 μl of this solution were added per well (100 μl) of each plate at subsequent days. Incubation period with MTT was 3 hours at 37° C. After incubation, the plates were centrifuged, and the medium was removed to a residual volume of 50 μl per well. Then, 100 μl of DMSO were added, and the plates were shaken for 1 hour. Absorbance was measured at a wavelength of 580 nm.

REFERENCES

[a] Mosmann T; Rapid colorimetric assay for cellular growth and survival: application to proliferation and cytotoxicity assay; *J. Immunol. Methods* 1983, 65: 55-63

[b] Bernhardt G, Reile H, Birnbock H, Spruss T, Schönenberger H. Standardized kinetic microassay to quantify differential chemosensitivity on the basis of proliferative activity. *J. Cancer Res. Clin. Oncol.* 1992, 118: 35-43

Cytotoxicity of Bendamustine Mofetil Ester

Eight different human cancer cell lines were treated according to the above general procedure for comparative determination of cytotoxicity of bendamustine-HCl and bendamustine mofetil ester. The results of this comparative cytotoxicity testing are summarized in Table 1 below:

TABLE 1

Comparison of the IC$_{50}$ values (errors as 95% confidence intervals) of bendamustine-HCl and bendamustine mofetil ester after long-term exposure (96 h) of different human cancer cell types

| Cell line | Tumour entity | ATCC-code | IC$_{50}$ bendamustine-HCl [μM] | IC$_{50}$ bendamustine mofetil ester [μM] | ratio |
|---|---|---|---|---|---|
| Jurkat[a] | Acute T-cell leukemia | TIB-152 | 42.6 ± 5.6 | 4.2 ± 0.3 | 10.1 |
| HEL92.1.7[a] | Erythroleukemia | TIB-180 | 84.0 ± 7.7 | 3.4 ± 0.4 | 24.7 |
| U-937[a] | Histocytic lymphoma | CRL-1593.2 | 91.9 ± 16.4 | 4.2 ± 0.9 | 21.9 |
| MG-63[b] | Osteosarcoma | CRL-1427 | 55 ± 3.3 | 3.4 ± 0.7 | 16.2 |
| SK-ES1[a] | Ewing sarcoma | HTB-86 | 11.0 ± 1.6 | 0.9 ± 0.2 | 12.2 |
| LnCap clone FGC[a] | Prostate cancer (metastasis of a subclavicular lymph node) | CRL-1740 | 71.6 ± 5.4 | 2.1 ± 0.6 | 34.1 |

TABLE 1-continued

Comparison of the $IC_{50}$ values (errors as 95% confidence intervals) of bendamustine-HCl and bendamustine mofetil ester after long-term exposure (96 h) of different human cancer cell types

| Cell line | Tumour entity | ATCC-code | $IC_{50}$ bendamustine-HCl [μM] | $IC_{50}$ bendamustine mofetil ester [μM] | ratio |
|---|---|---|---|---|---|
| Capan-1[b] | Pancreatic carcinoma | HTB-80 | 25.2 ± 5.4 | 1.3 ± 0.3 | 19.4 |
| NCl-H460[b] | Large cell bronchial carcinoma | HTB-177 | 89.5 ± 10.4 | 8.6 ± 0.6 | 10.4 |

[a]Investigated in the MTT assay (ref.: Mosmann T; Rapid colorimetric assay for cellular growth and survival: application to proliferation and cytotoxicity assay; *J. Immunol. Methods* 1983, 65: 55-63)
[b]Investigated in the crystal violet assay (ref.: Bernhardt G, Reile H, Birnbock H, Spruss T, Schönenberger H. Standardized kinetic microassay to quantify differential chemosensitivity on the basis of proliferative activity. *J. Cancer Res. Clin. Oncol.* 1992, 118: 35-43)

As becomes obvious from the experimental data listed in Table 1 above, bendamustine mofetil ester shows remarkably enhanced cytotoxicity compared to bendamustine-HCl against all human malignant tumour cell lines investigated.

The invention claimed is:

1. A compound of formula I

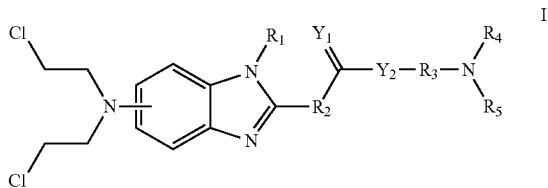

or a pharmaceutically acceptable salt thereof,
wherein $R_1$ is C1-C3 alkyl, $R_2$ and $R_3$ independently from each other represent C1-C3 alkanediyl, $Y_1$ and $Y_2$ represent oxygen, and $R_4$ and $R_5$ form a 5- to 7-membered ring structure together with the nitrogen located between $R_4$ and R5, wherein the ring structure is selected from the group consisting of pyrrolidine, piperidine, piperazine and morpholino wherein the atoms of the ring structure formed by $R_4$ and $R_5$ together with the nitrogen located between $R_4$ and $R_5$ are unsubstituted, or substituted with a substituent selected from the group consisting of C1-C4 alkyl, C1-C4 alkoxy, C1-C4 alkylsulfide, unsubstituted amino (—NH$_2$) and dialkylamino in which alkyl is C1-C4 alkyl.

2. The compound according to claim 1, wherein $R_1$ is methyl, $R_2$ is propanediyl, $R_3$ is ethanediyl, $Y_1$ and $Y_2$ represent oxygen, and $R_4$ and $R_5$ form a morpholino moiety together with the nitrogen located between $R_4$ and $R_5$.

3. A pharmaceutical composition comprising the compound of claim 1 or a pharmaceutically acceptable salt thereof as a pharmaceutically active agent, and at least one pharmaceutically acceptable excipient.

4. The pharmaceutical composition according to claim 3, wherein the pharmaceutical composition is free of non-ionic surfactant(s) selected from the group consisting of polyethoxylated castor oil or derivatives thereof, block copolymer of ethylene oxide and propylene oxide and free of saccharide(s) selected from the group consisting of monosaccharide(s), disaccharide(s), oligo saccharide(s), cyclic oligosaccharide(s), polysaccharide(s) and saccharide alcohol(s).

5. The compound of claim 1, wherein the ring structure is selected from the group consisting of piperazine and morpholino.

6. The compound of claim 5, wherein the ring structure is morpholino.

7. The compound of claim 1, wherein the ring structure is unsubstituted.

8. The compound of claim 1, wherein the ring structure is substituted and the substituent is selected from the group consisting of C1-C4 alkyl and C1-C4 alkoxy.

* * * * *

UNITED STATES PATENT AND TRADEMARK OFFICE
CERTIFICATE OF CORRECTION

PATENT NO. : 8,809,549 B2  
APPLICATION NO. : 13/870759  
DATED : August 19, 2014  
INVENTOR(S) : Schickaneder et al.

Page 1 of 1

It is certified that error appears in the above-identified patent and that said Letters Patent is hereby corrected as shown below:

On the title page, item (71), in "Applicant", in column 1, line 1, delete "Arevipharma GmbH, Radebuel (DE)" and insert --Dr. Helmut Schickaneder (DE); Christian Schickaneder (DE)--, therefor In the Claims, Column 20, line 34, in Claim 4, delete "oligo saccharide(s)" and insert --oligosaccharide(s)--, therefor Signed and Sealed this  
Twenty-third Day of December, 2014

Michelle K. Lee  
*Deputy Director of the United States Patent and Trademark Office*